(12) United States Patent
Arnaud et al.

(10) Patent No.: US 6,326,012 B1
(45) Date of Patent: Dec. 4, 2001

(54) TRANSFER-RESISTANT MAKE-UP OR CARE COMPOSITION BASED ON ISOPARAFFINS AND FUNCTIONALIZED SYNTHETIC WAXES

(75) Inventors: Pascal Arnaud, L'Hay les Roses; Frederic Auguste, Chevilly Larus, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/371,007

(22) Filed: Aug. 10, 1999

(30) Foreign Application Priority Data

Aug. 10, 1998 (FR) .................................................. 98 10255

(51) Int. Cl.7 ............................... A61K 7/00; A61K 7/48; A61K 7/035; A61K 7/027; A61K 7/031
(52) U.S. Cl. ................... 424/401; 424/78.02; 424/78.03; 424/63; 424/64; 514/772.3
(58) Field of Search .................. 424/63, 64, 401, 424/78.02, 78.03; 514/772.3

(56) References Cited

U.S. PATENT DOCUMENTS

| 5,505,937 | * | 4/1996 | Castrogiovanni et al. | 424/63 |
| 5,955,003 | * | 9/1999 | Terren et al. | 424/401 |
| 6,071,503 | * | 6/2000 | Drechsler et al. | 424/64 |
| 6,143,308 | * | 11/2000 | Vanstraceele et al. | 424/401 |

FOREIGN PATENT DOCUMENTS

| 0 709 083 | 1/1996 | (EP) . |
| 0 847 752 | 6/1998 | (EP) . |
| 0 850 644 | 7/1998 | (EP) . |
| WO 96/15761 | 5/1996 | (WO) . |
| WO 96/40044 | 12/1996 | (WO) . |

OTHER PUBLICATIONS

Araki Hiromitsu, "Nonaqueous Makeup Cosmetic", Patent Abstracts of Japan, vol. 10, No. 131 & JP 60 255714, 1985.

* cited by examiner

Primary Examiner—Dana Dudash
Assistant Examiner—Mina Haghighatian
(74) Attorney, Agent, or Firm—Oblon, Spivak, McClelland, Maier & Neustadt, P.C.

(57) ABSTRACT

A solid transfer-resistant make-up or care composition containing, in a physiologically acceptable medium:
  at least one volatile hydrocarbon based oil, and
  as a hardening agent, at least one functionalized synthetic wax having at least one hydroxyl or carboxyl functional group and having a melting point of between 75° C. and 120° C. and
  Hansen Solubility Parameters, $\delta_d$, $\delta_h$ such that:

$15.50 \leq \delta_d \leq 18.50$ $(J/cm^3)^{1/2}$, $4.50 \leq \delta_a \leq 7.50$ $(J/cm^3)^{1/2}$, wherein $\delta_a = (\delta_p^2 + \delta_h^2)^{1/2}$.

18 Claims, No Drawings

TRANSFER-RESISTANT MAKE-UP OR CARE COMPOSITION BASED ON ISOPARAFFINS AND FUNCTIONALIZED SYNTHETIC WAXES

BACKGROUND OF THE INVENTION

1. Field of the Invention

The present invention relates to a transfer-resistant make-up or care composition for the skin, keratin fibers (eyelashes, eyebrows or hair) or the lips, containing a combination of a volatile hydrocarbon-based oil and a functionalized synthetic wax, to the use of this combination to give transfer-resistance properties to make-up or care compositions for the skin, keratin fibers or the lips, as well as to a process for manufacturing such transfer-resistant make-up or care compositions.

2. Background of the Invention

The development of so-called "transfer-resistant" make-up or care products is currently the subject of considerable cosmetic research. These products, for example foundations, lipsticks, eyeshadows or face powders, are distinguished by the fact that once they have been applied to the skin or the lips, they are not appreciably deposited on other surfaces with which they come into contact, e.g., glass, cup, cigarettes or clothing.

A first approach for preventing the transfer of applied cosmetic products involves coating them with a layer of products well-known for their anti-adhesive properties, such as fluoro products or silicone products. However, formulations of this type have the drawback of being relatively unsuitable for cosmetic use. For example, the film of lipstick becomes oily and liable to migrate onto the skin adjacent to the lips and the eyelids.

Another possibility for obtaining transfer-resistant products involves using silicone polymers or resins in combination with volatile starting materials which, after evaporation of the latter, leave an inert film which is resistant to transfer onto other surfaces, The volatile starting materials used are, for example, cyclic silicones of very low viscosity (less than 3 centistokes) or isoparaffins.

In order for these make-up products to be in solid form, it is necessary to add hardening compounds thereto, such as waxes. Problems then arise with respect to mechanical stability and/or of compatibility between the waxes and the volatile products. Specifically, for low wax contents, the stick is found to be not sufficiently hard, which may be the cause of stability problems or problems during use. Simply increasing the proportion of hardening waxes does not solve these problems since it is generally reflected by a degradation in the cosmetic properties of the product, which becomes uncomfortable to wear.

SUMMARY OF THE INVENTION

An object of the present invention was to find waxes which allow sufficient hardening, i.e., which have maximum gelling power, so as to limit the proportion of these waxes in the transfer-resistant solid cosmetic products and to avoid the problems of incompatibility. The transfer problem applies to skincare or skin treatment products containing both colored and non-colored active agents.

The Inventors have found, unexpectedly, that a particular class of hydrocarbon-based waxes characterized by a specific melting range and specific solubility parameters allows the problems described above to be solved.

The use of such waxes to gel volatile liquid silicone vehicles such as cyclomethicones for the purpose of preparing cream-deodorants is described in document WO 97/17942, but in no way relates to the production of a solid isoparaffin-based transfer-resistant product.

Accordingly, the object of the invention, and others, may be accomplished with a transfer-resistant cosmetic make-up or care composition for the skin, the lips or keratin fibers, comprising at least one volatile hydrocarbon-based oil and at least one functionalized synthetic wax which satisfies the melting point criteria and Solubility parameters defined below.

The object of the invention may also be accomplished with the use of synthetic waxes which satisfy the melting point criteria and solubility parameters mentioned below, to harden make-up or care compositions for the skin, the lips and keratin fibers, containing volatile hydrocarbon-based oils, in order to obtain solid transfer-resistant cosmetic compositions.

The object of the invention may also be accomplished with a process for preparing solid transfer-resistant makeup or care compositions combining volatile hydrocarbon-based oils and synthetic waxes having the properties below.

The object of the invention may also be accomplished with a process for limiting the transfer of a make-up or care composition for the skin, the lips or keratin fibers onto a surface with which the skin, the lips or the keratin fibers are placed in contact, this process consisting in introducing the combination of hydrocarbon-based oils and synthetic waxes as defined below into the composition.

A more complete appreciation of the invention and many of the attendant advantages thereof will be readily obtained as the same becomes better understood by reference to the following detailed description.

DETAILED DESCRIPTION OF THE INVENTION

The solid transfer-resistant cosmetic compositions of the present invention thus comprise, in a fatty phase, at least one volatile hydrocarbon-based oil and at least one functionalized synthetic wax, i.e., a wax bearing at least one hydroxyl or carboxyl functional group and having a melting point of between 75° C. and 120° C. and Hansen Solubility parameters ($\delta_d$, $\delta_p$ and $\delta_h$) such that:

$$15.50 \leq \delta_d \leq 18.50 (J/cm^3)^{1/2},$$

and $$4.50 \leq \delta_a \leq 7.50 (J/cm^3)^{1/2},$$

with $$\delta_a = (\delta_p^2 + \delta_h^2)^{1/2},$$

In the present invention, the term "volatile oil" refers to an oil which can evaporate at room temperature from a support onto which it has been applied, in other words an oil which has a measurable vapor pressure at room temperature, and the term "volatile hydrocarbon-based oil" refers to an oil whose skeleton contains only hydrogens and carbons.

The preferred volatile hydrocarbon-based oils suitable for use in the present invention are, in particular, isoparaffins, i.e., branched alkanes comprising from 8 to 16 carbon atoms. Mixtures of such isoparaffins can also be used.

The volatile hydrocarbon-based oil most preferably used for the present invention is isododecane, i.e. 2,2,4,4,6-pentamethylheptane. An example of an isododecane available on the market which may be mentioned is the product sold under the name Permethyl® 99A by Presperse Inc.

The functionalized synthetic waxes used for the gelation and hardening of the make-up compositions of the present invention comprise at least one hydroxyl or carboxyl group and are defined by their melting point and by their solubility parameters in three-dimensional solubility space according to Hansen (*The three-dimensional solubility parameters*, J. Paint Technol., 39, page 105 (1967), incorporated herein by reference in its entirety).

Synthetic waxes have the advantage of being products of constant composition and of having a constant fatty alcohol or fatty acid content, unlike waxes of natural origin.

According to Hansen, the change in internal energy during vaporization is considered as being the sum of three contributions, the first due to the hydrogen bonds (h index), the second due to the dipolar interactions (p index) and the third due to dispersion forces (d index).

The Solubility parameter $\delta$ (defined as the square root of the change in internal energy per unit of volume of the chemical species during its vaporization and expressed in $(J/cm^3)^{1/2}$ is defined as a vector of coordinates ($\delta_h, \delta_p$ and $\delta_d$), the amplitude of the vector being given by $$\delta^2 = \delta_h^2 + \delta_p^2 + \delta_d^2$$

The parameter $\delta_a$ used in the present invention as a criterion for selecting the appropriate waxes is defined by the following equation:

$$\delta_a = (\delta_p^2 + \delta_h^2)^{1/2}$$

The gelling power of the synthetic waxes of the present invention is associated with the compatibility/incompatibility phenomena of these waxes with the fatty phase, in particular with the isoalkanes.

Waxes with a $\delta_a$ parameter of less than 4.5 are too compatible with isoalkanes and consequently have insufficient gelling and structuring power. On the other hand, a parameter $\delta_a$ of greater than 7.5 signals excessive incompatibility between the wax and the isoalkanes, which is reflected by demixing and in homogeneity phenomena and possibly by a lack of mechanical stability.

In one preferred embodiment of the present invention, the waxes satisfying these selection criteria are linear fatty alcohols with a very long chain corresponding to the following chemical formula

$$CH_3-(CH_2)_n-CH_2OH \quad (1)$$

where n is an integer ranging from 18 to 58.

Such $C_{20-60}$ fatty alcohols are commercially available, for example from New Phase Technologies under the names Performacol® 350, Performacole® 425, Performacole® 550 and Performacol® 700, or from Petrolite under the names Unilin®, 350 Alcohol, Unilin® 425 Alcohol, Unilin® 550 Alcohol and Aniline 700 Alcohol. These are mixtures of linear alcohols containing very long chains, obtained by a polymerization process for obtaining polymers with a very low polydispersity index ($M_p/M_n \approx 1.1$). Their weight-average molar mass is approximately between 350 and 1000.

In the transfer-resistant make-up compositions of the present invention, the volatile hydrocarbon-based oil generally represents from 5 to 90%, preferably from 5 to 80% and better still from 10 to 60% by weight, of the total cosmetic composition. These ranges include all specific values and subranges therebetween, such as 8, 15, 20, 25, 30, 40, 50 and 70% by weight. These hydrocarbon-based oils can represent 100% of the volatile phase present in the composition.

The functionalized synthetic wax(es) generally represent(s) from 5% to 30% and preferably from 8% to 20% by weight of the total composition. These ranges include all specific values and subranges therebetween, including 10, 12, 15 and 25% by weight.

Besides volatile hydrocarbon-based oils, the fatty phase in the cosmetic compositions of the present invention can also comprise in particular, $C_{8-16}$ isoparaffins, and the functionalized synthetic waxes defined above, one or more waxes of animal, plant or synthetic origin other than the $C_{20-60}$ fatty alcohols and fatty acids described above, preferably having a melting point of greater than 30° C. and ideally greater than 45° C. These waxes are chosen, inter alia, from optionally hydrogenated, hydroxylated or acetylated lanolin, beeswax, spermaceti, lanolin alcohols, lanolin fatty acids and acetylated lanolin alcohol, camauba wax, candelilla wax, kapok wax, Ouricury wax, rice wax, hydrogenated jojoba wax, alfalfa wax, Japan wax, cork fibre wax or sugarcane wax, cocoa butter, paraffin wax, lignite wax, petrolatum wax, petroleum jelly wax or microcrystalline waxes, ceresin, ozokerite, montan wax, polyethylene waxes, the waxes obtained by Fischer-Tropech synthesis, linear esters resulting from the reaction of a saturated $C_{10-40}$ carboxylic acid and a saturated $C_{10-40}$ alcohol, cetyl alcohol, stearyl alcohol, calcium lanolates or stearates and hydrogenated castor, palm, coconut, sunflower or copra oil.

They can also contain one or more additional volatile solvents other than the volatile hydrocarbon-based oils of the present invention. Examples of these additional volatile solvents include the oils of volatile cyclic silicones such as cyclomethicones ($D_4$, $D_5$, $D_6$), volatile linear silicones such as decamethyltetrasiloxane ($L_4$), octylheptamethyltrisiloxane, octemethyitrisilaxane ($L_3$), hexylheptamethyltrisiloxane and volatile fluoro oils such as nonafluoromethoxybutane or perfluoromethylcyclopentane.

These volatile solvents preferably represent from 0 to 50% by weight of the volatile phase. This range includes all specific values and subranges therebetween, such as 0.1, 0.2, 0.5, 1, 2, 5, 10, 20, 25, 30 and 40% by weight of the volatile phase.

The compositions of the present invention may also contain non-volatile silicone and/or hydrocarbon-based and/or fluoro oils, silicone gums and silicone waxes.

The non-volatile silicone oils which can be used in the composition according to the invention can be oils of low viscosity such as linear polysiloxanes, the degree of polymerization of which is preferably from 6 to 2000 approximately. Examples include polydimethylsilaxanes (PDMS) with a viscosity of greater than 10 mPa·s, phenyldimethicones, phenyltrimethicones and polyphenylmethylsilaxanes, and mixtures thereof.

The silicone gums which can be used in the product of the invention may be polysiloxanes of high molecular mass, ranging from 200,000 to 1,000,000, and having a viscosity of greater than 500,000 mPa·s. They can be used alone or as a mixture with a solvent such as a polydimethylsiloxane or polyphenylsiloxane oil.

The gums may be present in a proportion of from 0 to 2% by weight of active material in the final cost product, preferably in a proportion of from 0.1 to 1%. These ranges include all specific values and subranges therebetween, such as 0.01, 0.02, 0.05, 0.2, 0.5, 0.75, 1.25, 1.50 and 1.75% by weight.

The silicone waxes which can be used in the composition according to the invention can be substituted linear polysiloxanes. Mention may be made, for example, of polyether-silicone waxes and alkyl- or alkoxydimethicones containing from 16 to 45 carbon atoms. These silicone waxes can be present in a proportion of from 0 to 18% by weight in the final composition, preferably in a proportion of from 2 to 15%. These ranges include all specific values and subranges therebetween, such as 0.01, 0.02, 0.05, 0.1, 0.2, 0.5, 1, 5, 10 and 12% by weight.

The hydrocarbon-based oils which can be used in the composition according to the invention can be oils of plant, animal, mineral or synthetic origin.

Examples of non-volatile hydrocarbon-based oils which can be used in the invention include:

hydrocarbon-based oils of animal origin, such as perhydrosqualene;

hydrocarbon-based plant oils, such as liquid triglycerides of fatty acids of 4 to 10 carbon atoms, such as heptanoic or octanoic acid triglycerides, or alternatively sunflower oil, corn oil, soybean oil, marrow oil, grapeseed oil, sesame oil, hazelnut oil, apricot oil, macadamia oil, castor oil, avocado oil, caprylic/capric acid triglycerides such as those sold by Stearineries Dubois or those sold under the names Miglyol 810, 812, and 818 by Dynamit Nobel, jojoba oil or karite butter;

linear or branched hydrocarbons of mineral or synthetic origin, such as petroleum jelly, polydecenes or hydrogenated polyisobutene such as parleam;

synthetic esters and ethers, such as oils of formula $R_1COOR_2$ in which $R_1$ represents a higher fatty acid residue comprising from 6 to 29 carbon atoms and $R_2$ represents a hydrocarbon-based chain containing from 3 to 30 carbon atoms, such as purcellin oil, isopropyl myristate, 2-ethylhexyl palpitate, 2-octyldodecyl stearate, 2-octyldodecyl erucate, isostearyl isostearate, arachidyl propionate, 2-octyldodecyl benzoate; hydroxylated esters such as isostearyl lactate, octyl hydroxystearate, octyldodecyl hydroxystearate, diisostearyl malate, triisocetyl citrate; polyol esters such as propylene glycol dioctanoate, neopentyl glycol dibeptancate, diethylene glycol diisononanoate and pentaerythritol esters; and fatty alcohols which are liquid at room temperature, containing a branched and/or unsaturated carbon-based chain containing from 12 to 24 carbon atoms, such as octyldodecanol, 2-hexyldecanol, 2-butyl-octanol, 2-undecylantadecanol, isostearyl oleyl alcohol; as well as mixtures thereof.

These non-volatile oils are preferably present in an amount ranging from 5 to 60% by weight of the total composition. This range includes all specific values and subranges therebetween, such as 8, 10, 12, 15, 20, 25, 30, 40 and 50% by weight of the total composition.

As will be readily appreciated by one skilled in the art, the transfer-resistant cosmetic compositions can also contain active agents which give them their characteristic cosmetic properties and cosmetic adjuvants. These are, for example, substances such as sunscreens, free-radical scavengers, hydrating agents, vitamins, proteins, ceramides, pH regulators, antioxidants, preserving agents, fillers, pigments, dyes, emollients, antifoaming agents, fragrances, surfactants and plasticizers.

As will be readily appreciated by one skilled in the art, a person skilled in the art will take care to select the above optional additional compound(s) and the amount thereof such that the advantageous properties intrinsically associated with the cosmetic composition of the invention are not, or are not substantially, adversely affected by the addition(s) envisaged.

The composition of the invention preferably contains a particulate phase generally present in a proportion of from 0.05 to 35% of the total weight of the composition, preferably from 2 to 25%, and which can comprise pigments and/or nacres and/or fillers usually used in cosmetic compositions. These ranges include all specific values and subranges therebetween, such as This filler can give a colored, white or colorless composition.

The term "pigments" refers to white or colored, inorganic or organic particles which are insoluble in the liquid fatty phase and are intended to color and/or opacity the cast product. The term "fillers" should be understood as meaning colorless or white, inorganic or synthetic, lamellar or non-lamellar particles. The term "nacres" refers to iridescent particles produced in particular by certain molluscs in their shell, or else synthesized. These fillers and nacres serve in particular co modify the texture of the composition.

The pigments can be present in the composition in a proportion of from 0.05 to 25% of the weight of the final composition, and preferably in a proportion of from 0.05 to 15%. These ranges include all specific values and subranges therebetween, such as Examples of inorganic pigments which can be used in the invention include titanium oxide, zirconium oxide or cerium oxide, as well as zinc oxide, iron oxide or chromium oxide and ferric blue. Examples of organic pigments which can be used in the invention, include carbon black and barium, strontium, calcium (DC Red No. 7) and aluminum lakes.

The nacres can be present in the composition in a proportion of from 0 to 20% of the total weight of the cast product, preferably in a proportion ranging from 1 to 15%. These ranges include all specific values and subranges therebetween, such as Among the nacres which can be used in the invention, mention may be made of mica coated with titanium oxide, with iron oxide, with natural pigment or with bismuth oxychloride, such as coiffured titanium mica.

The fillers can be present in a proportion of from 0 to 35% of the total weight of the composition, preferably 2 to 15%. These ranges include all specific values and subranges therebetween, such as 0.1, 0.2, 0.5, 1, 5, 10, 15, 25 and 30% by weight. Mention may be made in particular of talc, mica, silica, kaolin, nylon (in particular Orgasol) powder, polyethylene powder, Teflon, starch, boron nitride, copolymer microspheres such as Expancel (Nobel Industries), Polytrap (Dow Corning) and silicone resin microbeads (Tospearl from Toshiba, for example).

The composition can also comprise a surfactant, for example a common anionic or nonionic surfactant. The surfactant is preferably present in a proportion of from 0.5 to 8% by weight of the composition. These ranges include all specific values and subranges therebetween, such as 1, 2, 3, 5 and 6% by weight.

The composition may also comprise liposoluble dyes and/or water-soluble dyes.

The cosmetic compositions of the invention can be in a solid or pasty form which does not flow under its own weight. These can be anhydrous compositions or emulsions.

The form which best exploits the hardening properties of the category of waxes used in the present invention is, of course, the stick form or the form cast in a dish. Consequently, this is a preferred embodiment of the present of the present invention.

The processes for manufacturing the make-up or care products according to the invention do not differ in any way from the processes conventionally used in cosmetics and are entirely familiar to those skilled in the art.

A solid cast make-up product such as a lipstick, a solid foundation or a concealer, or alternatively a product for coloring or protecting the skin or a "cake" of mascara or a compact powder, are i manufactured, for example, by melting and mixing together the non-volatile components of the composition, adding the volatile phase at a lower temperature, casting the mixture thus obtained in a mold of suitable shape, and cooling to room temperature.

Having generally described this invention, a further understanding can be obtained by reference to certain specific examples which are provided herein for purposes of illustration only and are not intended to be limiting unless otherwise specified.

EXAMPLES

Example 1

Evaluation of the hardness of a composition containing the isododecane+wax combination Various sticks axe prepared from a typical composition consisting of 85% by weight of isododecane (Permethyl® 99A from Presperse) and 15% of a wax whose chemical nature varies from one stick to another. The sticks are manufactured by melting and mixing these two components together, casting in a suitable cylindrical mould and cooling. The hardness of the sticks obtained is measured at 20° C. using a DFGHS 2 dynanometer from the company Indelco Chatillon, traveling at a speed of 100 mm/minute. It is expressed as the shear force (expressed in grams) required to cleave a stick 12.7 mm in diameter under these conditions.

Table 1 below shows the various waxes used, their melting point, the Solubility parameters $\delta_d$ and $\delta_a$ and the results obtained from the hardness tests.

TABLE 1

| Wax | m.p. (° C.) | $\delta_d$ ($J^{1/2}$ cm$^{-3/2}$) | $\delta_a$ ($J^{1/2}$ cm$^{-3/2}$) | shear force (g) |
|---|---|---|---|---|
| Performalene 500 polyethylene wax (New Phase Technologies) | 86 | 16.29 | 0 | 6 |
| Performalene 655 polyethylene wax (New Phase Technologies) | 102 | 16.35 | 0 | 6 |
| Kester Wax 82H octanosyl stearate (Koster Keunen) | 82 | 16.52 | 3.07 | 4 |
| Performacol 700 linear fatty alcohol (New Phase Technologies) | 105 | 16.58 | 4.62 | 73 |
| Performacol 550 linear fatty alcohol (New Phase Technologies) | 99 | 16.54 | 4.73 | 75 |
| Performacol 425 linear fatty alcohol (New Phase Technologies) | 91 | 16.51 | 5.55 | 28 |
| Elfacos C26 hydroxyoctacosanyl hydroxystearate (Akzo Nobel) | 80 | 16.75 | 7.9 | 1 |
| Cutina HR hydrogenated caster oil (Henkel) | 86 | 16.96 | 9.01 | incompatible |

These hardness test results show that only the waxes according to the present invention, i.e. those with a $\delta_a$ parameter of between 4.5 and 7.5 $J^{1/2}/cm^{3/2}$ produce sticks of sufficient hardness.

Although having a melting point and a $\delta_d$ parameter within the ranges defined in the present invention, the other waxes give sticks which are too soft or which have incompatibility problems.

Example 2

Various sticks were prepared in the manner indicated in Example 1, using the following typical composition:

| | |
|---|---|
| wax (see Table 2) | 16 g |
| isododecane (Permethyl ® 99A, Presperse) | 38.8 g |
| ozokerite (Ozakerite Wax SP 1020, Strahl Pitsch) | 6.4 g |
| volatile silicone (DC 200 Fluid 1.5 cSt, Dow Corning) | 38.8 g |
| | 100 g |

The hardness of the sticks is measured at 20° C. using a TA-XT2 texture analyser sold by Rheo.

The hardness is likened to the maximum force (in Newtons) measured during the penetration of a stainless steel cylinder 5 mm in diameter to a depth of 0.3 mm and at a speed of 0.1 mm/second into a stick to be tested.

The results obtained are collated in Table 2 below.

TABLE 2

| Wax | m.p. (° C.) | $\delta_d$ ($J^{1/2}$ cm$^{-3/2}$) | $\delta_a$ ($J^{1/2}$ cm$^{-3/2}$) | F max (N) |
|---|---|---|---|---|
| Performalene ® 500 polyethylene wax (New Phase Technologies) | 86 | 16.29 | 0 | 0.17 |
| A-C 1702 polyethylene wax (Allied Chemical) | 92 | 16.3 | 0 | not measurable too soft <0.17 |
| Performacol ® 550 linear fatty alcohol (New Phase Technologies | 99 | 16.54 | 4.73 | 3.23 |

These results show that the synthetic waxes according to the present invention satisfactorily harden a complex composition capable of constituting the base of a transfer-resistant make-up product, whereas waxes not in accordance with the invention, since they do not have a solubility parameter $\delta_a$ within the range defined above, give compositions whose mechanical strength is unsatisfactory.

Example 3

Lipsticks

The following transfer-resistant lipsticks A, B and C in stick form are prepared:

| | A | B Comparative | C Comparative |
|---|---|---|---|
| Performacol ® 550 linear fatty alcohol (New Phase Technologies) | 10.00 | — | — |
| Performalene ® 500 polyethylene wax (New Phase Technologies) | | 10.00 | 23.00 |
| isododecane | 40.00 | 40.00 | 33.61 |
| cyclopentapolysiloxane | 10.00 | 10.00 | 8.39 |
| hydrogenated polyisobutene | 31.34 | 31.34 | 26.34 |
| | 2.90 | 2.90 | 2.90 |

-continued

|  | A | B Comparative | C Comparative |
|---|---|---|---|
| DC Red No. 7 Calcium lake | 1.80 | 1.80 | 1.80 |
| titanium oxide | 3.30 | 3.30 | 3.30 |
| FD & C Yellow No. 6 Aluminum lake | 0.06 | 0.06 | 0.06 |
| black iron oxide | 0.60 | 0.60 | 0.60 |
| DC Red No. 21 Aluminum lake | 100% by weight | 100% by weight | 100% by weight |
| Shear force (in grams) | 70 | 8 | 75 |

Comparison of compositions A and B shows that, for a given wax content, only the fatty alcohol Performacol® 550 in accordance with the invention gives a lipstick of satisfactory hardness.

To achieve a comparable hardness with a wax not in accordance with the invention, it is necessary to increase the wax content considerably (composition C). However, increasing the wax content is reflected by deterioration in the cosmetic properties of the stick of lipstick. Specifically, composition A is considerably more slippery, less dry and more uniform than composition C.

Obviously, numerous modifications and variations of the present invention are possible in light of the above teachings. It is therefore to be understood that within the scope of the appended claims, the invention may be practiced otherwise than as specifically described herein.

The present application is based on French Patent Application Serial No. 98-10255, filed on Aug. 10, 1998, and incorporated herein by reference in its entirety.

What is claimed is:

1. A solid transfer-resistant make-up or care composition, comprising, in a physiologically acceptable medium:
   at least one volatile hydrocarbon-based oil, and
   as a hardening agent, at least one functionalized synthetic wax having at least one hydroxyl or carboxyl functional group and having a melting point of between 75° C. and 120° C., and
   Hansen Solubility Parameters, $\delta^d$, $\delta_p$ and $\delta_h$, such that:

$$15.50 \leq \delta_d \leq 18.50 \ (J/cm^3)^{1/2},$$

and $$4.50 \leq \delta_a \leq 7.50 \ (J/cm^3)^{1/2},$$

wherein $$\delta_a = (\delta_p^2 + \delta_h^2)^{1/2}.$$

2. The solid transfer-resistant composition of claim 1, wherein the volatile hydrocarbon-based oil is a $C_{8-16}$ isoparaffin or a mixture of $C_{8-16}$ isoparaffins.

3. The solid transfer-resistant composition of claim 2, wherein the volatile hydrocarbon-based oil is isododecane (2,2,4,4,6-pentamethylheptane).

4. The solid transfer-resistant composition of claim 1, wherein the flinctionalized synthetic wax is a linear $C_{20-60}$ fatty alcohol.

5. The solid transfer-resistant composition of claim 1, comprising 5 to 90% by weight of the volatile hydrocarbon-based oil.

6. The solid transfer-resistant composition of claim 1, comprising 5 to 30% by weight of the functionalized synthetic wax.

7. The solid transfer-resistant composition of claim 1, further comprising one or more waxes of animal, plant or synthetic origin in addition to the functionalized synthetic wax.

8. The solid transfer-resistant composition of claim 1, further comprising one or more volatile solvents in addition to the volatile hydrocarbon-based oil.

9. The solid transfer-resistant composition of claim 1, comprising a silicone gum.

10. The solid transfer-resistant composition of claim 9, comprising at most 2% by weight of the silicone gum.

11. The solid transfer-resistant composition of claim 1, further comprising at least one non-volatile oil of plant, animal, mineral or synthetic origin.

12. The solid transfer-resistant composition of claim 11, comprising 5 to 60% by weight of the non-volatile oil.

13. The solid transfer-resistant composition of claim 1, further comprising one or more cosmetic adjuvants or active agents selected from the group consisting of sunscreens, free-radical scavengers, hydrating agents, vitamins, proteins, ceramides, pH regulators, antioxidants, preserving agents, fillers, pigments, dyes, emollients, antifoaming agents, fragrances, surfactants, and plasticizers.

14. The solid transfer resistant composition of claim 1, which is in the form of a solid or pasty make-up or care product, which is in anhydrous or emulsion form.

15. The solid transfer-resistant composition of claim 14, which is a make-up product and is a lipstick, a foundation, an eyeshadow, a face powder or a mascara.

16. The solid transfer-resistant composition of claim 14, which is a solid make-up product and is a stick of lipstick, a foundation or a compact powder.

17. A method of preparing the composition of claim 1, comprising combining the volatile hydrocarbon-based oil and the functionalized synthetic wax.

18. A method of increasing the transfer resistance of a make-up or care composition for the skin, comprising incorporating the composition of claim 1 into a make-up or care composition for the skin.

* * * * *